United States Patent [19]
Wada et al.

[11] Patent Number: 4,900,352
[45] Date of Patent: Feb. 13, 1990

[54] 2-PHENOXYPYIMIDINE DERIVATIVE AND HERBICIDAL COMPOSITION

[75] Inventors: Nobuhide Wada; Yoshihiro Saito, both of Iwata; Shoji Kusano, Hamamatsu; Yasuhumi Toyokawa; Takeshige Miyazawa, both of Ogasa; Ikuo Kajiwara, Nagaokakyo; Satoru Takahashi, Ogasa, all of Japan

[73] Assignees: Kumiai Chemical Industry Co., Ltd.; Ihara Chemical Industry Co., Ltd., both of Tokyo, Japan

[21] Appl. No.: 291,353

[22] Filed: Dec. 29, 1988

Related U.S. Application Data

[63] Continuation of Ser. No. 37,323, Apr. 13, 1987, abandoned.

[30] Foreign Application Priority Data

Jun. 6, 1986 [JP] Japan ................. 60-131285

[51] Int. Cl.[4] .................. A01N 43/54; C07D 239/34; C07D 239/52; C07D 239/60
[52] U.S. Cl. ........................ 71/92; 544/299; 544/303; 544/301; 544/302; 544/309; 544/311; 544/312; 544/313; 544/314; 544/315; 544/316; 544/318
[58] Field of Search ............... 544/300, 303, 304, 309, 544/313, 225, 299, 301, 302; 71/92

[56] References Cited

U.S. PATENT DOCUMENTS

| | | | |
|---|---|---|---|
| 3,126,271 | 3/1964 | Thomson et al. | 71/92 |
| 4,409,017 | 10/1983 | Serban et al. | 546/142 |
| 4,427,437 | 1/1984 | Serban et al. | 71/92 |
| 4,626,275 | 12/1986 | Rempfler | 71/94 |

FOREIGN PATENT DOCUMENTS

| | | |
|---|---|---|
| 1187 | 3/1979 | European Pat. Off. |
| 8192 | 2/1980 | European Pat. Off. |
| 2030981 | 1/1971 | Fed. Rep. of Germany |
| 9474 | 5/1967 | Japan |
| 117486 | 9/1979 | Japan |

OTHER PUBLICATIONS

Bruszewski, CA 93-8032C (1980).
"4-(4-chlorophenyl)-4-hydroxypiperidine." Khuthier et al., CA 106-175530g (1987) "Studies of Tertiery Amine Oxides, 9, Thermal rearrangement of 1-(4-substituted) phenylpiperidine N-oxides to the corresponding N-hydroxylamines".
"Syntheses and Herbicidal Activities of Phenoxypyrimidines and Phenoxytriazines", Agr. Biol. Chem. vol. 30, No. 9, pp. 896-905, 1966.
Chem. Abstracts, vol. 94, No. 13, p. 752 (Mar. 30, 1981) Abstract No. 103416 (k).

*Primary Examiner*—Mukund J. Shah
*Assistant Examiner*—Cecilia Shen
*Attorney, Agent, or Firm*—Oblon, Spivak, McClelland, Maier & Neustadt

[57] ABSTRACT

A 2-phenoxypyrimidine derivative having the formula:

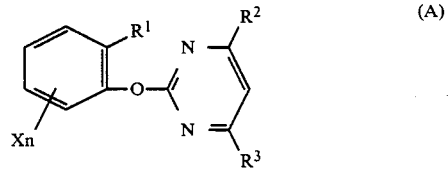

wherein $R^1$ is a formyl group, a dimethoxymethyl group or $-COOR^4$ (wherein $R^4$ is a hydrogen atom, a lower alkyl group, a benzyl group, an alkali metal atom, an alkaline earth metal atom or an organic ammonium group), $R^2$ is a chlorine atom, a methyl group, a methoxy group or a difluoromethoxy group, $R^3$ is a methyl group or a methoxy group, X is a halogen atom, a lower alkyl group, a lower alkoxy group, an amino group, a hydroxyl group, a nitro group or a cyano group, and n is 1 or 2.

11 Claims, No Drawings

2-PHENOXYPYIMIDINE DERIVATIVE AND HERBICIDAL COMPOSITION

This application is a Continuation of application Ser. No. 07/037,323, filed on Apr. 13, 1987, now abandoned.

The present invention relates to novel 2-phenoxypyrimidine derivatives, processes for their production, herbicidal compositions containing them, and a method for their application as herbicides to paddy rice fields, upland fields and non-agricultural fields.

It is disclosed that some 2-phenoxypyrimidine derivatives have herbicidal activities, for instance, in (1) Arg. Biol. Chem. Vol. 30, No. 9, p. 896 (1966), (2) Japanese Unexamined Patent Publication No. 55729/1979, (3) Japanese Unexamined Patent Publication No. 117486/1979 and (4) Japanese Examined Patent Publication No. 9474/1967.

However, the compounds disclosed in such publications and literature have no adequate herbicidal effects against annual weeds, and they exhibit no substantial herbicidal activities against perennial weeds.

The present inventors have conducted extensive research on 2-phenoxypyrimidine compounds with an aim to develop a compound having excellent herbicidal activities, and as a result, have found that the compounds of the present invention with substituents introduced to certain specific positions on the pyrimidine and benzene rings exhibit excellent herbicidal effects at a relatively low dose not only against annual weeds but also against perennial weeds, particularly against purple nutsedge (*Cyperus rotundus*) and johnsongrass (*Sorghum halepense*), and at the same time, they have a high level of safety against crop plants such as cotton (*Gossypium hirsutum*), rice plant (*Oryza sativa*), wheat (*Triticum aestivum*) or soybean (*Glycine max*), and are effective not only the major weeds grown in such crop plants fields but also against generally hardly controllable weeds. The compounds of the present invention have a feature that their toxicity against human beings and animals is very low while their herbicidal activities are very high. The present invention has been accomplished on the basis of these discoveries.

The present invention provides a 2-phenoxypyrimidine derivative having the formula:

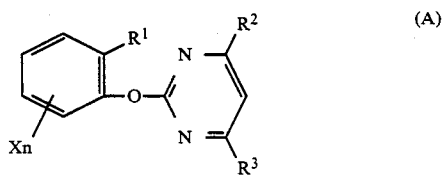

wherein $R^1$ is a formyl group, a dimethoxymethyl group or —COOR$^4$ (wherein $R^4$ is a hydrogen atom, a lower alkyl group, a benzyl group, an alkali metal atom, an alkaline earth metal atom or an organic ammonium group), $R^2$ is a chlorine atom, a methyl group, a methoxy group or a difluoromethoxy group, $R^3$ is a methyl group or a methoxy group, X is a halogen atom, a lower alkyl group, a lower alkoxy group, an amino group, a hydroxyl group, a nitro group or a cyano group, and n is 1 or 2.

The compound of the formula A can be prepared by a process which comprises reacting a compound of the formula:

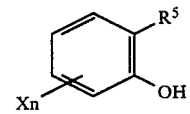

wherein $R^5$ is a formyl group, a dimethoxymethyl group or —COOR$^6$ (wherein $R^6$ is a hydrogen atom, a lower alkyl group or a benzyl group), and X and n are as defined above, with a pyrimidine compound of the formula:

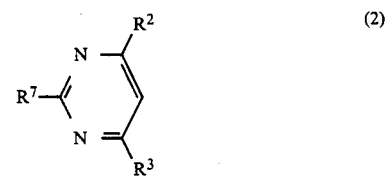

wherein $R^2$ and $R^3$ are as defined above, and $R^7$ is a halogen atom, an alkylsulfonyl group, an unsubstituted benzylsulfonyl group or a substituted benzylsulfonyl group, to obtain a compound of the formula:

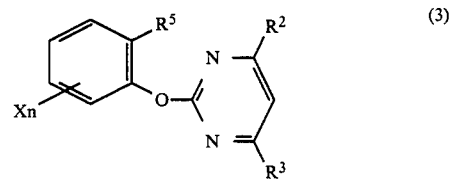

wherein $R^2$, $R^3$, $R^5$, X and n are as defined above, or reacting a compound of the formula:

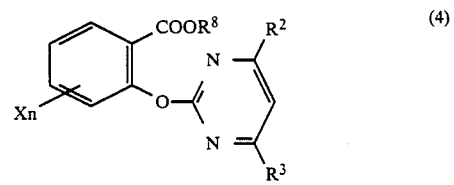

wherein $R^2$, $R^3$, X and n are as defined above, and $R^8$ is a lower alkyl group or a benzyl group, with an alkali metal or alkaline earth metal base, to obtain a compound of the formula:

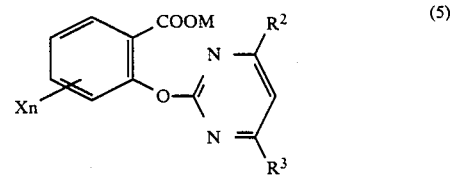

wherein $R^2$, $R^3$, X and n are as defined above and M is an alkali metal atom or an alkaline earth metal atom; or treating a compound of the formula 5 as defined above, with an acid to obtain a compound of the formula:

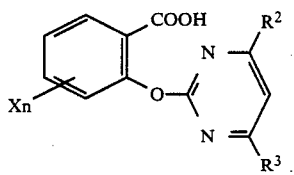

(6)

wherein $R^2$, $R^3$, X and n are as defined above; or catalytically reducing a compound of the formula 4 wherein $R^8$ is a benzyl group, to obtain a compound of the formula 6 as defined above; or reacting a compound of the formula:

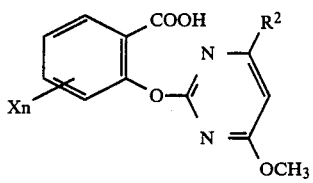

(7)

wherein $R^2$, X and n are as defined above, with a base to obtain a compound of the formula:

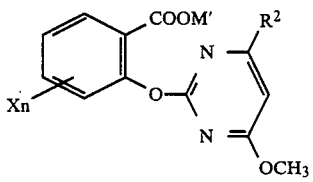

(8)

wherein $R^2$, X and n are as defined above, and M' is an alkali metal atom, an alkaline earth metal atom, or an organic ammonium group.

The present invention also provides a herbicidal composition comprising a herbicidally effective amount of the 2-phenoxypyrimidine derivative of the formula A and an agricultural adjuvant.

Further, the present invention provides a method for killing weeds which comprises applying a herbicidally effective amount of a 2-phenoxypyrimidine derivative of the formula A.

Now, the present invention will be described in detail with reference to the preferred embodiments.

In this specification, the lower alkyl group means an alkyl group having from 1 to 6 carbon atoms, preferably from 1 to 4 carbon atoms, which may be a straight chain or branched alkyl group, such as methyl, ethyl, n-propyl, i-propyl, n-butyl, i-butyl, t-butyl, n-pentyl, i-pentyl, n-hexyl or i-hexyl.

Likewise, the lower alkoxy group means an alkoxy group having from 1 to 6 carbon atoms, preferably from 1 to 4 carbon atoms, such as methoxy, ethoxy, n-propoxy, i-propoxy, n-butoxy, t-butoxy or n-hexyloxy.

In a preferred embodiment, $R^2$ is a chlorine atom, a difluoromethoxy group, a methyl group or a methoxy group, and $R^3$ is a methoxy group. More preferably, each of $R^2$ and $R^3$ is a methoxy group.

More specifically, it is preferred that $R^1$ is $-COOR_4$ (wherein $R^4$ is a hydrogen atom, a $C_1-C_5$ alkyl group or a benzyl group) X is a $C_1-C_5$ alkyl group, a $C_1-C_5$ alkoxy group, a halogen atom or a nitro group, and each of $R^2$ and $R^3$ is a methoxy group. When n is 2, it is preferred that one X is located at 6-position and another X is located at 3-, 4- or 5-position. When n is 1, X is preferably located at 6-position. X is preferably a halogen atom, a $C_1-C_5$ alkyl group, or a $C_1-C_5$ alkoxy group.

In a specific preferred embodiment, n is 2, X is a chlorine atom or a methyl group, $R^1$ is $-COOH$, and each of $R^2$ and $R^3$ is a methoxy group.

In another specific preferred embodiment, n is 1, X is a chlorine atom at 6-position, $R^1$ is $-COOR$ (wherein R is a hydrogen atom or a $C_1-C_5$ alkyl group), and each of $R^2$ and $R^3$ is a methoxy group.

In a further specific preferred embodiment, n is 1, X is a $C_1-C_4$ alkoxy group at 6-position, $R^1$ is $-COOH$, and each of $R^2$ and $R^3$ is a methoxy group.

Now, specific examples of the compound of the present invention will be presented in Table 1. Compound numbers given in the Table will be referred to in the subsequent description in the specification.

TABLE 1

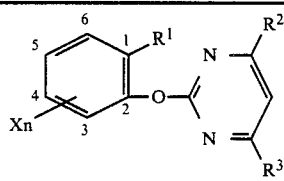

| Compound No. | $R^1$ | $R^2$ | $R^3$ | Xn | Melting point (°C.) or refractive index $n_D^{20}$ |
| --- | --- | --- | --- | --- | --- |
| 1 | COOH | $OCH_3$ | $OCH_3$ | 3-$CH_3$ | 125–129° C. |
| 2 | " | " | " | 3-$OCH_3$ | 179–181° C. |
| 3 | " | " | " | 3-F | 154–157° C. |
| 4 | " | " | " | 4-$CH_3$ | 154–157° C. |
| 5 | " | " | " | 4-Cl | 131–135° C. |
| 6 | " | " | " | 4-$OCH_3$ | 118–121° C. |
| 7 | " | " | " | 4-F | 147–150° C. |
| 8 | " | " | " | 4-$NO_2$ | 93–96° C. |
| 9 | " | " | " | 5-$CH_3$ | 159–162° C. |
| 10 | " | " | " | 5-$OCH_3$ | 157–159° C. |
| 11 | " | " | " | 5-Br | 141–144° C. |
| 12 | " | " | " | 5-Cl | 130–132° C. |
| 13 | " | " | " | 5-F | 118–121° C. |
| 14 | " | " | " | 5-I | 164–167° C. |
| 15 | " | " | " | 5-$OC_3H_7$—i | 124–133° C. |

TABLE 1-continued

| Compound No. | $R^1$ | $R^2$ | $R^3$ | Xn | Melting point (°C.) or refractive index $n_D^{20}$ |
|---|---|---|---|---|---|
| 16 | " | " | " | 5-$C_2H_5$ | 141–143° C. |
| 17 | " | " | " | 5-$C_3H_7$—i | 125–129° C. |
| 18 | " | " | " | 5-CN | 141–144° C. |
| 19 | COOH | $OCH_3$ | $OCH_3$ | 6-F | 133–134° C. |
| 20 | " | " | " | 6-Cl | 123–126° C. |
| 21 | " | Cl | " | 6-F | 104–108° C. |
| 22 | " | $OCHF_2$ | " | " | 137–139° C. |
| 23 | " | $CH_3$ | " | " | 106–109° C. |
| 24 | " | $OCH_3$ | " | 3,5-$Cl_2$ | 122–125° C. |
| 25 | " | " | " | 3-$CH_3$,5-Cl | 148–151° C. |
| 26 | " | " | " | 5,6-$F_2$ | 142–145° C. |
| 27 | $COOCH_3$ | Cl | " | 3-$CH_3$ | 102–104° C. |
| 28 | " | $OCH_3$ | " | " | 76–78° C. |
| 29 | " | " | " | 3-$OCH_3$ | 105–116° C. |
| 30 | " | " | " | 3-F | 88–91° C. |
| 31 | " | " | " | 3-Cl | 92–96° C. |
| 32 | " | Cl | " | 4-$CH_3$ | 73–74° C. |
| 33 | " | $OCH_3$ | " | " | 55–57° C. |
| 34 | " | " | " | 4-Cl | 49–50° C. |
| 35 | " | " | " | 4-$OCH_3$ | 65–69° C. |
| 36 | " | " | " | 4-F | 61–63° C. |
| 37 | " | " | " | 4-$NH_2$ | 106–108° C. |
| 38 | " | " | " | 4-$NO_2$ | 94–97° C. |
| 39 | " | Cl | " | 4-Cl | 108–109° C. |
| 40 | " | " | " | 5-Cl | 1.5746 |
| 41 | $COOCH_3$ | Cl | $OCH_3$ | 5-$CH_3$ | 72–74° C. |
| 42 | " | $OCH_3$ | " | 5-$NH_2$ | 1.5820 |
| 43 | " | " | " | 5-F | 1.5300 |
| 44 | " | " | " | 5-Cl | 56–59° C. |
| 45 | " | " | " | 5-$CH_3$ | 1.5469 |
| 46 | " | " | " | 5-$OCH_3$ | 101–102° C. |
| 47 | " | " | " | 5-$NO_2$ | 76–78° C. |
| 48 | " | " | " | 5-Br | 82–83° C. |
| 49 | " | " | " | 5-I | 101–103° C. |
| 50 | " | " | " | 5-$OC_3H_7$—i | 40–45° C. |
| 51 | " | " | " | 5-$C_2H_5$ | 1.5349 |
| 52 | " | " | " | 5-$C_3H_7$—i | 1.5348 |
| 53 | " | " | " | 5-CN | 79–82° C. |
| 54 | " | " | " | 6-Cl | 55–56.5° C. |
| 55 | " | " | " | 6-$OCH_3$ | 93–99° C. |
| 56 | " | " | " | 6-F | 52–54° C. |
| 57 | " | " | " | 6-$CH_3$ | 76–79° C. |
| 58 | " | Cl | " | 6-F | 59–61° C. |
| 59 | " | $OCHF_2$ | " | 6-Cl | 1.5241 |
| 60 | " | " | " | 6-F | 1.5100 |
| 61 | " | $CH_3$ | " | " | 1.5400 |
| 62 | " | $OCH_3$ | " | 3-$CH_3$,5-Cl | 82–86° C. |
| 63 | $COOCH_3$ | $OCH_3$ | $OCH_3$ | 5,6-$F_2$ | 1.5260 |
| 64 | $COOC_2H_5$ | " | " | 6-OH | 1.5490 |
| 65 | " | " | " | 6-F | 1.5319 |
| 66 | " | Cl | " | " | 1.5438 |
| 67 | " | $OCH_3$ | " | 6-Cl | 1.5365 |
| 68 | " | " | " | 5-$C_3H_7$—i | 56–59° C. |
| 69 | $COOC_3H_7$—n | " | " | 6-F | 1.5261 |
| 70 | " | " | " | 6-Cl | 1.5370 |
| 71 | $COOCH_2C_6H_5$ | " | " | " | 86–88° C. |
| 72 | $-CH(OCH_3)_2$ | " | " | 3,5-$Cl_2$ | 82–83° C. |
| 73 | CHO | " | " | " | 132–133° C. |

TABLE 1-continued

[Structure: benzene ring with positions 1-6, R¹ at position 1, O at position 2 connected to C(=N-CR²=CR³-N=) ring, Xn at positions 3/4]

| Compound No. | R¹ | R² | R³ | Xn | Melting point (°C.) or refractive index $n_D^{20}$ |
|---|---|---|---|---|---|
| 74 | COOCH₃ | Cl | CH₃ | 6-F | 1.5570 |
| 75 | " | CH₃ | " | " | 1.5450 |
| 76 | COO.Na | OCH₃ | OCH₃ | 6-Cl | >300° C. |
| 77 | COO.1/2Ca | " | " | " | 188–191° C. |
| 78 | COO.NH₃C₃H₇—i | " | " | " | 127–130° C. |
| 79 | CO₂H | " | " | 5-NH₂ | 153–156° C. |
| 80 | " | " | " | 6-CH₃ | 119–120° C. |
| 81 | CO₂CH₂—Ph | " | " | 6-CH₃ | 54–56° C. |
| 82 | CO₂H | " | " | 6-OCH₃ | 138–140° C. |
| 83 | CO₂CH₂—Ph | " | " | 6-OCH₃ | 111–113° C. |
| 84 | CO₂CH₃ | OCH₃ | OCH₃ | 6-C₂H₅ | 1.5434 |
| 85 | CO₂H | " | " | " | 122–123° C. |
| 86 | CO₂CH₂—Ph | " | " | " | 1.5630 |
| 87 | CO₂H | " | " | 6-OC₂H₅ | 127–128° C. |
| 88 | CO₂CH₂—Ph | " | " | " | 93–96° C. |
| 89 | CO₂H | " | " | 6-OC₃H₇—i | 120–122° C. |
| 90 | CO₂CH₂—Ph | " | " | " | 1.5576 |
| 91 | CO₂H | " | " | 6-NO₂ | 125–128° C. |
| 92 | CO₂CH₃ | " | " | " | 79–83° C. |
| 93 | CO₂CH₂—Ph | " | " | " | 107–110° C. |
| 94 | CO₂H | " | " | 6-NH₂ | 149–152° C. |
| 95 | CO₂CH₂—Ph | " | " | 6-OC₃H₇—n | 1.5595 |
| 96 | CO₂H | " | " | " | 110–111° C. |

TABLE 1-continued

[Structure: phenyl ring with positions 1-6, R¹ at position 1, O-C(=N-)(N=) linkage at position 2 to a group with R² and R³, Xn substituent]

| Compound No. | R¹ | R² | R³ | Xn | Melting point (°C.) or refractive index $n_D^{20}$ |
|---|---|---|---|---|---|
| 97 | $CO_2CH_2$-Ph | " | " | 6-$OC_4H_9$—n | 1.5565 |
| 98 | $CO_2H$ | " | " | " | 107–108° C. |
| 99 | " | " | " | 5-$NO_2$ | 127–131° C. |
| 100 | $CO_2CH(CH_3)_2$ | " | " | 6-Cl | 1.5306 |
| 101 | $CO_2CH_2CH(CH_3)_2$ | " | " | " | 1.5275 |
| 102 | $CO_2C_4H_9$—n | " | " | " | 1.5382 |
| 103 | $CO_2CH(CH_3)$—$C_2H_5$ | $OCH_3$ | $OCH_3$ | 6-Cl | 1.5298 |
| 104 | $CO_2CH_2$-Ph | " | " | 6-$C_3H_7$—n | 33–34° C. |
| 105 | $CO_2H$ | " | " | " | 1.5419 |
| 106 | " | Cl | " | 6-Cl | 126–128° C. |
| 107 | CHO | " | " | " | 133–137° C. |
| 108 | $CO_2CH_2$-Ph | $OCH_3$ | " | 6-F | 1.5590 |
| 109 | CHO | " | " | 6-Cl | 122–123° C. |
| 110 | $CO_2CH_3$ | " | " | 6-Br | 1.6179 |
| 111 | $CO_2CH_2$-Ph | " | " | " | 72–75° C. |
| 112 | $CO_2H$ | " | " | " | 136–138° C. |
| 113 | $CO_2CH_3$ | " | " | 6-I | 1.5751 |
| 114 | $CO_2CH_2$-Ph | " | " | " | 1.5871 |
| 115 | $CO_2H$ | " | " | " | 138–141° C. |
| 116 | " | " | " | 3,6-$(CH_3)_2$ | 161–162° C. |
| 117 | " | " | " | 3-$CH_3$,6-Cl | 104–106° C. |
| 118 | $CO_2CH_2$-Ph | " | " | " | 83–84° C. |
| 119 | $CO_2CH_3$ | " | " | " | 1.5398 |

TABLE 1-continued

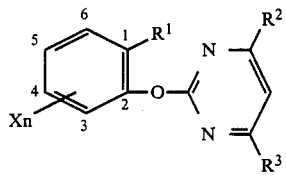

| Compound No. | R¹ | R² | R³ | Xn | Melting point (°C.) or refractive index $n_D^{20}$ |
|---|---|---|---|---|---|
| 120 | CO₂C₃H₇—n | " | " | " | 103–104° C. |
| 121 | CO₂H | " | " | 6-CH₃,5-Cl | 127–130° C. |
| 122 | " | " | " | 6-CH₃,3-OCH₃ | 136–137° C. |
| 123 | " | " | " | 5,6-Cl₂ | 143–144° C. |
| 124 | CO₂CH₃ | OCH₃ | OCH₃ | 6-NH₂ | 101–103° C. |
| 125 | CO₂CH₂—C₆H₅ | " | " | 6-OH | 63–65° C. |
| 126 | CH(OCH₃)OCH₃ | " | " | 3-Cl | 73–75° C. |
| 127 | CHO | " | " | " | 91–93° C. |
| 128 | CO₂H | " | " | " | 151–152° C. |
| 129 | CO₂CH₃ | Cl | " | 6-Cl | 1.5674 |
| 130 | CO₂CH₂—C₆H₅ | " | " | 6-F | 101–103° C. |
| 131 | CO₂CH₃ | " | " | 3,6-Cl₂ | 106–107° C. |
| 132 | CO₂CH₂—C₆H₅ | OCH₃ | " | 3,6-(CH₃)₂ | 1.5645 |
| 133 | " | " | " | 6-CH₃,3-OCH₃ | 96–98° C. |
| 134 | " | " | " | 5,6-Cl₂ | 86–87° C. |
| 135 | CO₂CH₃ | " | " | 5,6-Cl₂ | 91–92° C. |

The compounds of the present invention can be produced by the following processes, but their production is not restricted to such specific processes.

PROCESS A

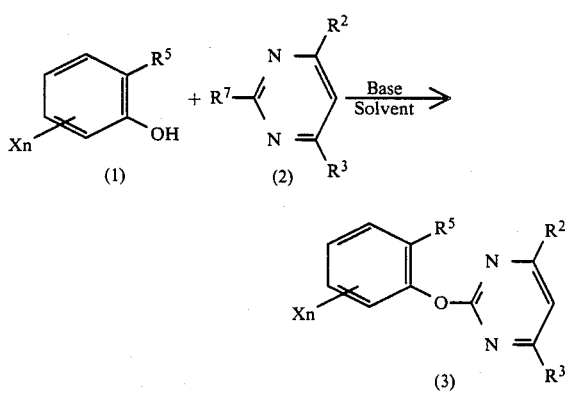

In the above formulas, R⁵ is a formyl group, a dimethoxymethyl group or —COOR⁶ (wherein R⁶ is a hydrogen atom, a lower alkyl group or a benzyl group), and R² and R³ are as defined above. R⁷ is a halogen atom, an alkylsulfonyl group, a benzylsulfonyl group or a substituted benzylsulfonyl group, and X and n are as defined above.

Among the compounds of the present invention, those represented by the formula 3 can be prepared by reacting the compound of the formula 1 and a pyrimidine compound of the formula 2 in the presence of a base, preferably in a solvent, within a temperature range from room temperature to the boiling point of the solvent, from 1 to 24 hours. When the reaction is conducted in the absence of a solvent, the reaction can be conducted within a temperature range from 120° to 160° C. by using a carbonate of an alkali metal, such as anhydrous potassium carbonate.

Here, as the solvent, there may be employed a hydrocarbon solvent such as benzene, toluene or xylene, a halogenated hydrocarbon solvent such as methylene chloride or chloroform, an alcohol solvent such as methanol, ethanol or isopropanol, an ether solvent such as ethyl ether, isopropyl ether, tetrahydrofuran or 1,4-dioxane, a ketone solvent such as acetone or methyl ethyl ketone, or ester solvent such as methyl acetate or ethyl acetate, an aprotic polar solvent such as dimethylformamide, dimethylacetamide or dimethylsulfoxide, and others such as acetonitrile or water. As the base, there may be employed an alkali metal such as sodium metal or potassium metal, an alkali metal or alkaline earth metal hydride such as sodium hydride, potassium hydride or calcium hydride, a carbonate such as sodium carbonate or potassium carbonate, or a metal hydroxide such as sodium hydroxide or potassium hydroxide.

PROCESS B

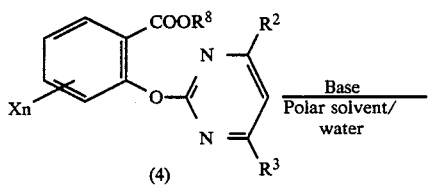

(4)

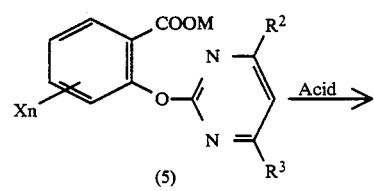

(5)

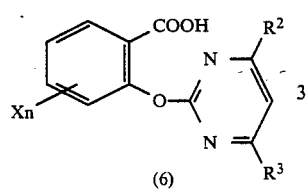

(6)

In the above formulas, $R^8$ is a lower alkyl group or a benzyl group, M is an alkali metal atom or an alkaline earth metal atom, and $R^2$, $R^3$, X and n are as defined above.

Among the compounds of the present invention, those represented by the formulas 5 and 6 can be prepared by reacting the compound of the formula 4 in the presence of a base in a polar solvent, in water or in a solvent mixture of a polar solvent and water within a temperature range from room temperature to the boiling point of the solvent from 0.5 to 36 hours to obtain a compound of the formula 5, which is then treated with an acid for precipitation to obtain a compound of the formula 6.

The solvent may be an alcohol solvent such as methanol, ethanol or isopropanol, or a ketone solvent such as acetone or methyl ethyl ketone. However, the solvent is not restricted to such examples. As the base, a carbonate such as sodium carbonate, potassium carbonate or calcium carbonate, or a metal hydroxide such as sodium hydroxide or potassium hydroxide may be employed.

Further, when $R^8$ in the formula 4 is a benzyl group, a compound of the formula 6 can be obtained by the catalytic reduction by means of hydrogenation.

PROCESS C

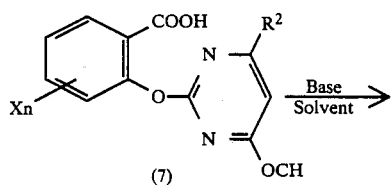

(7)

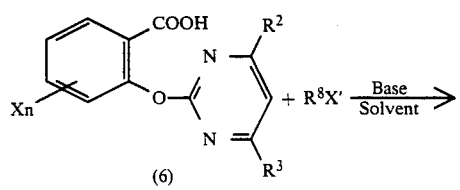

(8)

In the above formulas, $R^2$, X and n are as defined above, and M' is a cation such as an alkali metal, an alkaline earth metal or an organic ammonium group.

Among the compounds of the present invention, those represented by the formula 8 can be prepared by reacting the compound of the formula 7 with a base in the presence or absence of a solvent within a temperature range from room temperature to the boiling point of the solvent from 5 minutes to 10 hours.

Here, as the solvent, there may be mentioned a hydrocarbon solvent such as benzene, toluene or xylene, a halogenated hydrocarbon solvent such as methylene chloride or chloroform, an alcohol solvent such as methanol, ethanol or isopropanol, an ether solvent such as ethyl ether, isopropyl ether, tetrahydrofuran or 1,4-dioxane, a ketone solvent such as acetone or methyl ethyl ketone, an ester solvent such as methyl acetate or ethyl acetate, and others such as acetonitrile. The base may be an alkali metal such as sodium metal or potassium metal, an alkali metal or alkaline earth metal hydride such as sodium hydride, potassium hydride or calcium hydride, a carbonate such as sodium carbonate, potassium carbonate, or calcium carbonate, or a metal hydroxide such as sodium hydroxide or potassium hydroxidie. The organic base may be ammonia, an alkylamine (primary amine), a dialkylamine (secondary amine) or a trialkylamine (tertiary amine).

PROCESS D

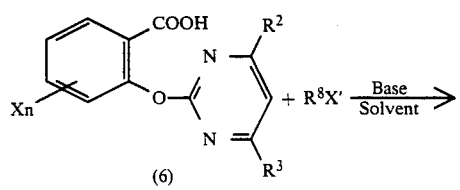

(6)

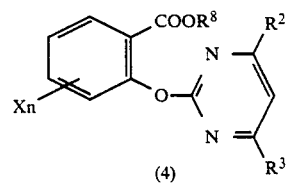

(4)

In the above formulas, $R^2$, $R^3$, $R^8$, X and n are as defined above, and X' is a halogen atom.

Among the compounds of the present invention, those represented by the formula 4 can be prepared by reaction the compound of the formula 6 with a base in the presence of a solvent within a temperature range of from room temperature to the boiling point of the solvent for from 1 to 24 hours.

Here, as the solvent, there may be mentioned a hydrocarbon solvent such as benzene, toluene or xylene, a halogenated hydrocarbon solvent such as methylene chloride or chloroform, an ether solvent such as ethyl ether, isopropyl ether, tetrahydrofuran or 1,4-dioxane, a ketone solvent such as acetone or methyl ethyl ketone, an ester solvent such as methyl acetate or ethyl acetate, an aprotic polar solvent such as dimethylformamide, dimethylacetamide or dimethylsulfoxide, and others such as acetonitrile. The base may be an alkali metal such as sodium metal or potassium metal, an alkali metal or alkaline earth metal hydride such as sodium hydride, potassium hydride or calcium hydride, a carbonate such as sodium carbonate, potassium carbonate, sodium hydrogencarbonate or potassium hydrogencarbonate, a metal hydroxide such as sodium hydroxide or potassium hydroxidie, or an organic base such as trialkylamine (tertiary amine) or pyridine.

Some of the compounds of the present invention can be precursors for the compounds of the present invention, and they may mutually be converted to each other. This relation may be illustrated as follows.

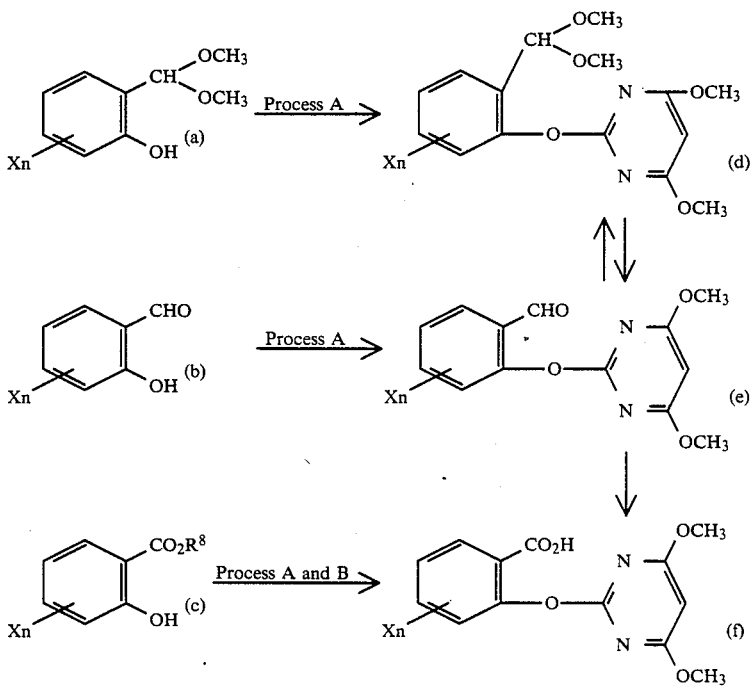

In the above formulas, $R^8$, X and n are as defined above.

The intermediates (a), (b) and (c) of the compounds of the present invention can be prepared in accordance with the methods disclosed in literatures. [References: Tetrahedron, 26, 4947 (1970), Berichte der Deutschen Chemischen Gesellschaft, 9, 423, 824 (1876), Annalen der Chemie, 113, 125 (1860), etc.]

The processes for the production from (a) to (d), from (b) to (e) and from (c) to (f) are as described for processes A and B. The compounds (d) and (e) can be converted to each other by an equbrium reaction. As a catalyst for this reaction, a protolytic acid such as hydrochloric acid, sulfuric acid or p-toluenesulfonic acid, or a Lewis acid such as titanium tetrachloride or aluminum chloride, may be employed. The conversion from (e) to (f) is an oxidation reaction, and as an oxidizing agent, oxygen, hydrogenperoxide, a permanganate, chromic acid or silver oxide, may be used.

Now, the present invention will be described in further detail with reference to Examples. However, it should be understood that the present invention is by no means restricted to such specific Examples.

EXAMPLE 1

Preparation of methyl 4-amino-2-(4,6-dimethoxypyrimidin-2-yl)oxy benzoate (Compound No. 37)

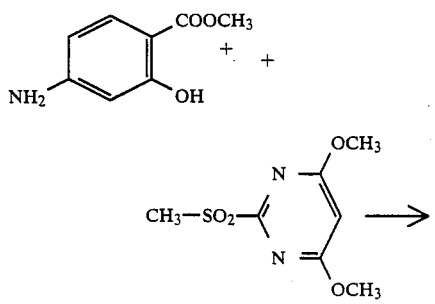

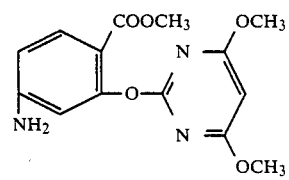

Ten ml of dimethylformamide was added to a suspension in toluene (100 ml) of methyl 4-aminosalicylate (7.7 g), 4,6-dimethoxy-2-methylsulfonylpyrimidine (10.1 g) and 60% sodium hydride (1.9 g), and the mixture was stirred at room temperature for 1 hour and then refluxed under heating for 10 hours. The reaction mixture was poured into water and extracted with ethyl acetate. The extract was washed with water and dried, and the solvent was distilled off under reduced pressure. The residue thus obtained was purified by silica gel column chromatography to obtain the above identified compound as a pale yellow crystal (8.0 g). (Melting point: 106°–108° C.)

EXAMPLE 2

Preparation of methyl 5-cyano-2-(4,6-dimethoxypyrimidin-2-yl)oxy benzoate (Compound No. 53)

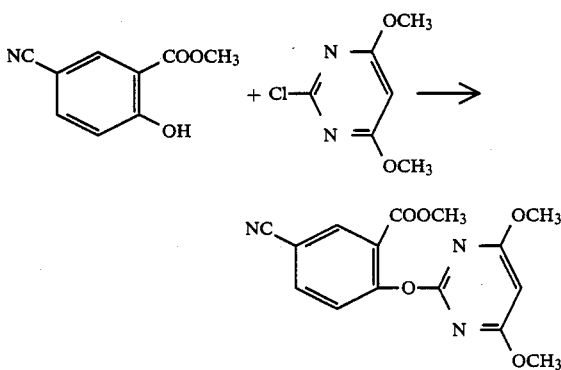

2-Chloro-4,6-dimethoxypyrimidine (0.5 g) was added to a suspension in dimethylformamide (7 ml) of methyl 5-cyanosalicylate (0.5 g) and 35% potassium hydride (0.15 g), and the mixture was reacted for 5 hours under reflux of dimethylformamide. The reaction mixture was poured into a large amount of water, and extracted with ethyl acetate. The extract was washed with water and dried, and the solvent was distilled off under reduced pressure. The residue thus obtained was purified by silica gel column chromatography to obtain the above identified compound as a white crystal (0.17 g). (Melting point: 79°–82° C.).

EXAMPLE 3

Preparation of methyl 2-(4-chloro-6-methoxypyrimidin-2-yl)oxy-5-methyl benzoate (Compound No. 41)

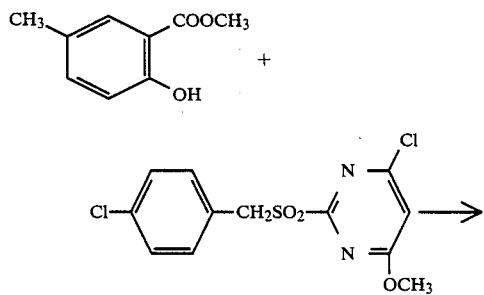

-continued

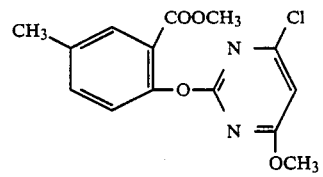

A methanol solution of 28% sodium methylate (2.3 g) was added to methyl 5-methylsalicylate (2.0 g), and methanol was distilled off under reduced pressure. Then, 2-(p-chlorobenzylsulfonyl)-4-chloro-6-methoxypyrimidine (4.0 g) in acetonitrile was introduced, and the mixture was refluxed for 3 hours under heating. The reaction mixture was poured into water, and extracted with toluene. The extract was washed with water and dried, and then the solvent was distilled off under reduced pressure. The residue thus obtained was purified by silica gel column chromatography to obtain the above identified compound as a white solid (1.3 g). (Melting point: 72°–74° C.)

EXAMPLE 4

Preparation of methyl 2-(4,6-dimethoxypyrimidin-2-yl)-oxy-6-methoxy benzoate (Compound No. 55)

Methyl 6-(4,6-dimethoxypyrimidin-2-yl)oxy salicylate (1.0 g) was dissolved in dimethylformamide (30 ml), and 60% sodium hydride (0.15 g) was added thereto. After the generation of hydrogen ceased, methyl iodide (1.0 g) was added thereto. The reaction mixture was reacted at a temperature of from 60° to 70° C. for 6 hours. Then, the reaction mixture was poured into water, and extracted with toluene. The extract was washed with water and dried, and the solvent was distilled off under reduced pressure. The residue thus obtained was purified by silica gel column chromatography to obtain the above identified compound as a yellow brown solid (0.8 g). (Melting point: 93°–99° C.)

EXAMPLE 5

Preparation of methyl 2-(4,6-dimethoxypyrimidin-2-yl)-oxy-6-fluorobenzoate (Compound No. 56)

4,6-Dimethoxy-2-methylsulfonylpyrimidine (4.0 g) was added to a solution in tetrahydrofuran (50 ml) of methyl 6-fluorosalicylate (3.5 g) and 60% sodium hydride (0.9 g), and the mixture was refluxed for 7 hours under heating. The reaction mixture was poured into water, and extracted with ethyl acetate. The extract was washed with water and dried, and the solvent was distilled off under reduced pressure. The residue thus obtained was purified by silica gel column chromatography to obtain the above identified compound as a white crystal (3.8 g). (Melting point: 52°–54° C.)

EXAMPLE 6

Preparation of methyl 5-chloro-2-(4,6-dimethoxypyrimidin-2-yl)oxy-3-methyl benzoate (Compound No. 62)

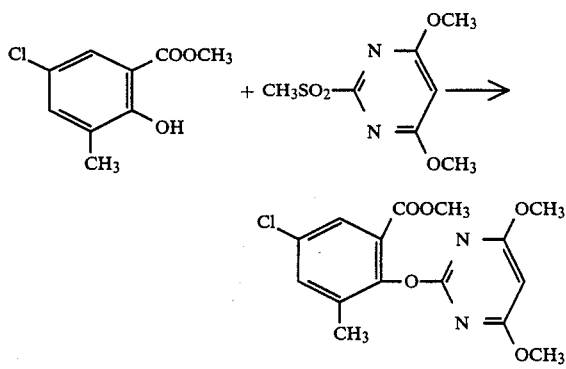

Methyl 5-chloro-3-methylsalicylate (5.3 g) and potassium t-butoxide (3.0 g) were put into dimethylformamide, and then 4,6-dimethoxy-2-methylsulfonylpyrimidine (5.8 g) was added thereto. The mixture was reacted at a temperature from 100° to 120° C. for 4 hours. The reaction mixture was poured into water, and extracted with toluene. The extract was washed with water and dried, and then the solvent was distilled off under reduced pressure. The crystal thus obtained was recrystallized from a solvent mixture of carbon tetrachloride and hexane to obtain the above identified compound as a slightly pink solid (4.1 g). (Melting point: 82°–86° C.)

EXAMPLE 7

Preparation of 2-(4,6-dimethoxypyrimidin-2-yl)oxy-4-nitrobenzoic acid (Compound No. 8)

To a suspension in ethanol (20 ml) of methyl 2-(4,6-dimethoxypyrimidin-2-yl)oxy-4-nitrobenzoate (2.4 g), an equimolar amount of an aqueous sodium hydroxide solution (20 ml) was added, and the mixture was reacted at room temperature for 12 hours under stirring. The reaction mixture was poured into water, and extracted with ethyl ether, and non-reacted starting materials were removed. Then, the aqueous phase was acidified with a 10% hydrochloric acid aqueous solution. This was extracted with ethyl ether. The extract was washed with water and dried, and then the solvent was distilled off under reduced pressure to obtain 1.8 g of a yellow crystal. This crystal was further washed with a mixture of hexane and isopropyl ether to obtain the above identified compound as a yellow crystal (1.7 g). (Melting point: 93°–96° C.)

EXAMPLE 8

Preparation of 2-(4,6-dimethoxypyrimidin-2-yl)oxy-6-fluorobenzoic acid (Compound No. 19)

To a solution in ethanol (10 ml) of methyl 2-(4,6-dimethoxypyrimidin-2-yl)oxy-6-fluorobenzoate (3.0 g), an equimolar amount of an aqueous sodium hydroxide solution (30 ml) was added, and the mixture was reacted at room temperature for 12 hours under stirring. The reaction mixture was poured into water, and extracted with ethyl ether, and non-reacted starting materials were removed. Then, the aqueous phase was acidified with a 10% hydrochloric acid aqueous solution. The aqueous solution was then extracted with ethyl ether. The extract was washed with water and dried, and then the solvent was distilled off under reduced pressure to obtain the above identified compound as a white crystal (1.5 g). (Melting point: 133°–134° C.)

EXAMPLE 9

Preparation of 2-chloro-6-(4,6-dimethoxypyrimidin-2-yl)oxy benzoic acid (Compound No. 20)

Benzyl 2-chloro-6-(4,6-dimethoxypyrimidin-2-yl)oxy benzoate (4.1 g) was added to a suspension comprising 10% Pd-C (0.7 g), methyl alcohol (160 ml) and acetic acid (30 ml), and the mixture was subjected to catalytic hydrogenation under atmospheric pressure. When the absorption of hydrogen ceased, the catalyst was filtered off, and the filtrate was concentrated. The residue thus obtained was dissolved in ethyl acetate, and washed with water and dried and concentrated to obtain 2.8 g of the above identified compound as a white crystal. (Melting point: 123°–126° C.)

EXAMPLE 10

Preparation of sodium 2-chloro-6-(4,6-dimethoxypyrimidin-2-yl)oxy benzoate (Compound No. 76)

A solution of 2-chloro-6-(4,6-dimethoxypyrimidin-2-yl)oxy benzoic acid (1.7 g) in tetrahydrofuran (10 ml) was gradually dropwise added at room temperature to a suspension of 60% sodium hydride (0.2 g) in tetrahydrofuran (20 ml), and the mixture was reacted for 30 minutes under stirring. After the completion of the reaction, isopropyl ether (30 ml) was added thereto, and the solid was collected by filtration. The solid was washed with 10 ml of each of tetrahydrofuran, isopropyl ether and hexane, and then dried to obtain the above identified compound (0.92 g). The melting point was 300° C. or higher.

The NMR spectrum (CDCl$_3$/DMSO-d$_6$, ppm) was as follows: 3.77(6H, s), 5.71 (1 H, s), 6.8–7.3 (3 H, m)

EXAMPLE 11

Preparation of 3,5-dichloro-2-(4,6-dimethoxypyrimidin-2-yl)oxy benzaldehyde (Compound No. 73)

3,5-Dichloro-2-(4,6-dimethoxypyrimidin-2-yl)oxy benzaldehyde dimethylacetal (2.1 g) was dissolved in acetic acid (50 ml), and then water (10 ml) and 35% hydrochloric acid (1 ml) were added thereto. The mixture was reacted at room temperature for 6 hours. The reaction mixture was poured into water, and extracted with toluene. The extract was washed with a 2% sodium hydroxide aqueous solution, and further washed 3 times with water. The toluene phase was dried, and concentrated under reduced pressure. The crystal thus obtained was recrystallized from a mixture of carbontetrachloride and hexane to obtain the above identified compound as a white crystal (1.0 g). (Melting point: 132°–133° C.)

EXAMPLE 12

Preparation of methyl 2-bromo-6-(4,6-dimethoxypyrimidin-2-yl)oxy benzoate (Compound No. 110)

A suspension of methyl 6-bromo salicylate (1.2 g), 4,6-dimethoxy-2-methylsulfonylpyrimidine (1.1 g) and potassium carbonate (0.7 g) in dimethylformamide (6 ml) was stirred at 100° C. for 1 hour. The reaction mixture was poured into water and extracted with ethyl acetate. This extract was washed with water and dried, and then the solvent was distilled off under reduced pressure. The residue thus obtained was purified by silica gel column chromatography to obtain the above identified compound as a colorless transparent viscous liquid (1.6 g). $n_D^{20}$: 1.6179

EXAMPLE 13

Preparation of propyl 6-chloro-2-(4,6-dimethoxypyrimidin-2-yl)oxy 3-methyl benzoate (Compound No. 120)

6-Chloro-2-(4,6-dimethoxypyrimidin-2-yl)oxy 3-methyl benzoic acid (1.49 g) and potassium hydrogen carbonate (0.62 g) were added to 10 ml of dimethylformamide, and the mixture was stirred at 80° C. for 10 minutes. Then, propyl bromide (0.6 g) was added thereto at the same temperature, and the mixture was reacted for 1 hour. The reaction mixture was poured into water, and extracted with ethyl acetate. The extract was washed with water and dried, and then the solvent was distilled off under reduced pressure to obtain the above identified compound as a white powder (1.2 g). (Melting point: 103°–104° C.)

EXAMPLE 14

Preparation of 3-chloro-2-(4,6-dimethoxypyrimidin-2-yl)oxy benzoic acid (Compound No. 128)

An aqueous solution of potassium permanganate (1.3 g) and disodium hydrogenphosphate (1 g) was dropwise added to a solution of 3-chloro-2-(4,6-dimethoxypyrimidin-2-yl)oxy benzaldehyde (1.7 g) in acetone (50 ml). The mixture was stirred at room temperature for 12 hours, and the precipitated manganese dioxide was filtered off. The filtrate was adjusted with hydrochloric acid to a pH of about 4 and then extracted with chloroform. The chloroform layer was washed with water and dried, and the solvent was distilled off under reduced pressure. The residue thus obtained was recrystallized from carbon tetrachloride to obtain the above identified compound as a white solid (1.1 g). (Melting point: 151°–152° C.).

The herbicidal composition of the present invention comprises a herbicidally effective amount of a 2-phenoxypyrimidine derivative of the present invention and an agricultural carrier or adjuvant.

When the compound of the present invention is used as a herbicide, the compound may be used as it is or as formulated in various formulations such as a wettable powder, a granule, an emulsifiable concentrate or a dust by blending it with a carrier, a surfactant, a dispersing agent or an adjuvant which is commonly employed for the formulation of agricultural chemicals.

As the carrier to be used for the formulation, there may be mentioned a solid carrier such as jeeklite, talc, bentonite, clay, kaolin, diatomaceous earth, white carbon, vermiculite, slaked lime, silica sand, ammonium sulfate or urea, or a liquid carrier such as isopropyl alcohol, xylene, cyclohexane or methyl naphthalene. As the surfactant and dispersing agent, there may be mentioned, for example, an alcohol-sulfuric acid ester, an alkyl aryl sulfonate, lignin sulfonate, a polyoxyethylene glycol ether, a polyoxyethylene alkyl aryl ether or a polyoxyethylene sorbitol mono-alkylate. As the adjuvant, for example, carboxymethyl cellulose, polyethylene glycol or gum arabic may be mentioned. In practical use, such a herbicide may be diluted to a suitable concentration before application, or may directly be applied.

The herbicide of the present invention may be used in combination with other herbicides. Examples of such other herbicides will be given below.

1-(α,α-dimethylbenzyl)-3-p-tolylurea,
2-chloro-4,6-bis(ethylamino)-1,3,5-triazine,
2-chloro-4-ethylamino-6-isopropylamino-1,3,5-triazine,
2-chloro-4,6-bis(isopropylamino)-1,3,5-triazine,
2,4-bis(ethylamino)-6-methylthio-1,3,5-triazine,
2,4-bis(isopropylamino)-6-methylthio-1,3,5-triazine,
methyl α-(4,6-dimethoxypyrimidin-2-yl carbamoylsulfamoyl)-0-toluylate,
1-[2-(2-chloroethoxy)phenylsulfamoyl]-3-(4-methoxy-6-methyl-1,3,5-triazin-2-yl)urea,
2-(1-ethoxyiminobutyl)-5-(2-ethylthiopropyl-3-hydroxycyclohex-2-enone
methyl 3-(1-allyloxyaminobutylidene)-6,6-dimethyl-2,4-dioxocyclohexane carboxylate sodium salt,
4-(2,4-dichlorobenzoyl)-1,3-dimethyl-5-pyrazolyl-p-toluenesulfonate,
3-isopropyl-2,1,3-benzothiadiazinone-(4)-2,2-dioxide,
N-(1-ethylpropyl)-3,4-dimethyl-2,6-dinitroaniline,
α-(2-naphtoxy)propionanilide,
N-(phosphonomethyl)glycidylisopropylamine salt,
2-benzothiazol-2-yloxy-N-methylacetanilide,
2-chloro-2′,6′-diethyl-N-(2-propoxyethyl)acetanilide,
2-chloro-2′-ethyl-N-(2-methoxy-1-methyl ethyl)-6′-methylacetanilide,
S-(2-methyl-1-piperidylecarbonylmethyl)-O,O-di-n-propyldithiophosphate,
2-methylthio-4-ethylamino-6-isopropylamino-1,3,5-triazine.

The herbicide of the present invention is capable of controlling various weeds in a paddy field by irrigated soil treatment before or after the emergence of weeds. Further, the herbicide is capable of controlling various weeds in an upland field by soil treatment before or after the emergence of weeds or by foliage treatment.

The dose of the active ingredient varies depending upon the field to be treated i.e. whether it is an agricultural field or non-agricultural field, the type of treatment, i.e. whether it is soil treatment or foliage treatment, the crop plants to be protected and the weeds to be killd. However, it is usually within a range of from 0.1 to 1,000 g/10 a, preferably from 0.5 to 500 g/10 a.

For instance, for soil treatment for an upland agricultural field, the dose of the active ingredient is usually from 0.5 to 500 g/10 a, although it depends on the crop plant and weeds to be killed.

For foliage treatment for an upland agricultural field, the dose is usually from 0.1 to 500 g/10 a. In the case of a non-agricultural field, the dose is usually from 1 to 1,000 g/10 a for soil or foliage treatment.

Now, Formulation Examples for the herbicidal composition of the present invention will be given. However, it should be understood that the present invention is by no means restricted to these specific Examples. In these Examples, "%" means "% by weight".

FORMULATION EXAMPLE 1 (wettable powder)

10% of Compound No. 1, 0.5% of Emulgen 810 (trademark, Kao Corporation), 0.5% of Demol N (trademark, Kao Corporation), 20% of Kunilite 201 (trademark, Kunimine Kogyo K.K.) and 69% of Jeeklite CA (tradename, Jeeklite Company Ltd.) were uniformly mixed and pulverized to obtain a wettable powder.

FORMULATION EXAMPLE 2 (emulsifiable concentrate)

30% of Compound No. 27, 20% of cyclohexanone, 11% of polyoxyethylene alkyl aryl ether, 4% of calcium alkylbenzenesulfonate and 35% of methyl naphthalene, were uniformly dissolved to obtain an emulsifiable concentrate.

FORMULATION EXAMPLE 3 (granule)

5% of Compound No. 3, 2% of a sodium salt of a lauryl alcohol-sulfuric acid ester, 5% of sodium lignin sulfonate, 2% of carboxymethyl cellulose and 86% of clay were uniformly mixed and pulverized. To 100 parts by weight of this mixture, 20 parts by weight of water was added, and the mixture was kneaded, and granulated into granules of from 14 to 32 mesh by means of an extrusion granulating machine, followed by drying to obtain granules.

FORMULATION EXAMPLE 4 (dust)

2% of Compound No. 54, 5% of diatomaceous earth and 93% of clay were uniformly mixed and pulverized to obtain a dust.

The compounds and the herbicidal compositions of the present invention are capable of effectively controlling annual weeds such as barnyardgrass (*Echinochloa crus-galli*), flatsedge (*Cyperus difformis*), monochoria (*Monochoria varinalis*), bulrush (*Scirpul hotarui*) and *Alisma canaliculatum*, and perennial weeds such as *Cyperus serotinus*, *Sagittaria pygmaea* and *Eleocharis kuroquwai*, grown in paddy fields. Further, they are capable of effectively controlling annual weeds such as barnyardglass (*Echinochloa crus-galli*), crabgrass (*Digitaria sanguinalis*), goosegrass (*Eleusine indica*), greenfoxtail (*Setaria viridis*), water foxtail (*Alopecurus aequalis*), annual bluegrass (*Poa annua*), wild oat (*Avena fatua*), italian ryegrass (*Lolium multiflorum*), smartweed (*Polygonum lapathifolium*), slender amaranth (*Amaranthus viridis*), lambsquarters (*Chenopodium album*), velvetleaf (*Abtilon theophrasti*), prickly sida (*Sida spinosa*), sicklepod (*Cassia tora*), chickweed (*Stellaria media*), morningglory (*Ipomoea spp*), common cocklebur (*Xanthium strumarium*), rice flatsedge (*Cyperus iria*), broadleaf signalgrass (*Brachiaria platyphylla*), itchgrass (*Rottoboellia exaltata*), downy brome (*Bromus tectorum*), wild buckwheat (*Polygonum convolvulus*), wild mustard (*Brassica arvensis*) and devils baggartickes (*Bidens frondosa*), and perennial weeds such as purple nutsedge (*Cyperus rotundus*), johnsongrass (*Sorghum halepense*), bermudagrass (*Cynodon dactylon*) and quackgrass (*Agropyron repens*) grown in upland fields. On the other hand, the safety to crop plants are extremely high. Further, the compounds of the present invention have a feature that as compared with the known compounds disclosed in the afore-mentioned publications and literature, the effects against perennial weeds such as purple nutsedge and johnsongrass are remarkable superior.

Now, the herbicidal activities of the herbicides of the present invention will be described with reference to Test Examples.

TEST EXAMPLE 1 (soil treatment)

In a 600 cm² pot filled with soil, seeds of barnyardgrass, crabgrass, smartweed, slender amarauth, lambsquater and rice flatsedge were sown and covered with soil of a thickness of from 0.5 to 1 cm. One day later from the seeding, a predetermined amount of a wettable powder prepared in accordance with Formulation Example 1, was diluted with water and applied to the soil surface at a rate of 100 liters per 10 ares. The evaluation was conducted on the 20th day after the treatment with the herbicide. The results were evaluated in accordance with the standards as identified in Table 2 and shown by the index numbers in Tables 3a and 3b.

TABLE 2

| Index No. | Herbicidal effects |
|---|---|
| 0 | No herbicidal effect |
| 1 | Herbicidal effect: more than 0% and less than 30% |
| 2 | Herbicidal effect: at least 30% and less than 50% |
| 3 | Herbicidal effect: at least 50% and less than 70% |
| 4 | Herbicidal effect: at least 70% and less than 90% |
| 5 | Herbicidal effect: more than 90% |

TABLE 3-a

| Compound No. | Dose of active ingredient (g/10a) | Ech | Dig | Pol | Ama | Che | Cyi |
|---|---|---|---|---|---|---|---|
| 1 | 400 | 5 | 3 | 3 | 5 | 5 | 5 |
| 2 | 400 | 3 | 2 | 0 | 5 | 4 | 5 |
| 3 | 400 | 5 | 5 | 5 | 5 | 5 | 5 |
| 7 | 400 | 3 | 2 | 2 | 5 | 2 | 3 |
| 8 | 400 | 4 | 5 | 5 | 5 | 5 | 5 |
| 9 | 400 | 5 | 3 | 1 | 5 | 5 | 5 |
| 10 | 400 | 5 | 5 | 5 | 5 | 5 | 5 |
| 11 | 400 | 2 | 3 | 4 | 5 | 4 | 4 |
| 12 | 400 | 3 | 3 | 5 | 5 | 5 | 5 |
| 13 | 400 | 5 | 5 | 5 | 5 | 5 | 5 |
| 14 | 400 | 2 | 1 | 1 | 5 | 3 | 5 |
| 15 | 400 | 5 | 5 | 5 | 5 | 1 | 5 |
| 16 | 400 | 3 | 3 | 5 | 5 | 4 | 5 |
| 17 | 400 | 2 | 3 | 5 | 4 | 0 | 3 |
| 18 | 400 | 3 | 3 | 4 | 5 | 4 | 3 |
| 19 | 400 | 5 | 5 | 5 | 5 | 5 | 5 |
| 20 | 400 | 5 | 5 | 5 | 5 | 5 | 5 |
| 21 | 400 | 5 | 5 | 5 | 5 | 5 | 5 |
| 22 | 400 | 5 | 5 | 5 | 5 | 5 | 5 |
| 23 | 400 | 4 | 4 | 3 | 5 | 5 | 4 |
| 24 | 400 | 2 | 0 | 5 | 4 | 2 | 5 |
| 25 | 400 | 3 | 2 | 5 | 5 | 4 | 5 |
| 26 | 400 | 5 | 5 | 5 | 5 | 5 | 5 |
| 28 | 400 | 5 | 5 | 5 | 5 | 5 | 5 |
| 29 | 400 | 4 | 3 | 2 | 5 | 5 | 5 |
| 30 | 400 | 5 | 5 | 5 | 5 | 5 | 5 |
| 31 | 400 | 5 | 5 | 5 | 5 | 5 | 5 |
| 33 | 400 | 4 | 2 | 3 | 4 | 5 | 5 |
| 36 | 400 | 5 | 4 | 4 | 5 | 2 | 4 |
| 37 | 400 | 0 | 3 | 4 | 5 | 4 | 5 |
| 38 | 400 | 0 | 4 | 4 | 5 | 3 | 4 |
| 42 | 400 | 4 | 5 | 2 | 4 | 4 | 5 |
| 43 | 400 | 5 | 5 | 4 | 5 | 5 | 5 |
| 44 | 400 | 5 | 4 | 3 | 5 | 4 | 5 |
| 45 | 400 | 3 | 0 | 1 | 5 | 4 | 5 |
| 46 | 400 | 5 | 4 | 5 | 5 | 5 | 5 |
| 47 | 400 | 5 | 5 | 5 | 5 | 5 | 5 |
| 48 | 400 | 2 | 2 | 2 | 4 | 4 | 5 |
| 49 | 400 | 2 | 2 | 2 | 5 | 2 | 4 |
| 50 | 400 | 5 | 5 | 5 | 5 | 3 | 5 |
| 51 | 400 | 2 | 3 | 4 | 5 | 0 | 3 |
| 52 | 400 | 1 | 2 | 4 | 4 | 2 | 4 |
| 53 | 400 | 4 | 4 | 5 | 5 | 5 | 5 |
| 54 | 400 | 5 | 5 | 5 | 5 | 5 | 5 |
| 56 | 400 | 5 | 5 | 5 | 5 | 5 | 5 |
| 57 | 400 | 5 | 5 | 5 | 5 | 5 | 5 |
| 58 | 400 | 5 | 5 | 5 | 5 | 4 | 5 |
| 59 | 400 | 5 | 5 | 5 | 5 | 5 | 4 |
| 60 | 400 | 5 | 5 | 5 | 5 | 5 | 5 |

TABLE 3-a-continued

| Compound No. | Dose of active ingredient (g/10a) | Ech | Dig | Pol | Ama | Che | Cyi |
|---|---|---|---|---|---|---|---|
| 61 | 400 | 2 | 3 | 2 | 5 | — | 5 |
| 62 | 400 | 4 | 3 | 5 | 5 | 4 | 5 |
| 63 | 400 | 5 | 5 | 5 | 5 | 5 | 5 |
| 65 | 400 | 5 | 5 | 5 | 5 | 5 | 5 |
| 66 | 400 | 5 | 5 | 5 | 5 | 5 | 5 |
| 67 | 400 | 5 | 5 | 5 | 5 | 5 | 5 |
| 68 | 400 | 2 | 3 | 4 | 5 | 1 | 4 |
| 69 | 400 | 5 | 5 | 5 | 5 | 5 | 5 |
| 70 | 400 | 5 | 5 | 5 | 5 | 5 | 5 |
| 71 | 400 | 5 | 5 | 5 | 5 | 5 | 5 |
| 72 | 400 | 2 | 1 | 5 | 4 | 5 | 5 |
| 73 | 400 | 1 | 1 | 5 | 4 | 3 | 5 |
| 74 | 400 | 4 | 4 | 2 | 4 | 2 | 4 |
| 75 | 400 | 3 | 4 | 5 | 5 | 3 | 5 |
| 76 | 400 | 5 | 5 | 5 | 5 | 5 | 5 |
| 77 | 400 | 5 | 5 | 5 | 5 | 5 | 5 |
| 78 | 400 | 5 | 5 | 5 | 5 | 5 | 5 |
| Comparative Compound A | 400 | 0 | 0 | 0 | 0 | 0 | 5 |
| Comparative Compound B | 400 | 0 | 0 | 0 | 0 | 2 | 5 |
| Comparative Compound C | 400 | 0 | 0 | 0 | 0 | 0 | 0 |

TABLE 3-b

| Compound No. | Dose of active ingredient (g/10a) | Ech | Dig | Pol | Ama | Che | Cyi |
|---|---|---|---|---|---|---|---|
| 79 | 400 | 3 | 4 | 5 | 5 | 5 | 5 |
| 80 | 400 | 5 | 5 | 5 | 5 | 5 | 5 |
| 81 | 400 | 5 | 5 | 5 | 5 | 5 | 5 |
| 82 | 400 | 5 | 5 | 5 | 5 | 5 | 5 |
| 83 | 400 | 2 | 4 | 3 | 5 | 5 | 5 |
| 84 | 400 | 5 | 5 | 5 | 5 | 5 | 5 |
| 85 | 400 | 5 | 5 | 5 | 5 | 5 | 5 |
| 86 | 400 | 5 | 5 | 5 | 5 | 5 | 5 |
| 87 | 400 | 5 | 5 | 5 | 5 | 5 | 5 |
| 88 | 400 | 3 | 4 | 5 | 5 | 5 | 5 |
| 89 | 400 | 5 | 5 | 5 | 5 | 5 | 5 |
| 90 | 400 | 2 | 4 | 4 | 5 | 4 | 5 |
| 91 | 400 | 5 | 5 | 5 | 5 | 5 | 5 |
| 92 | 400 | 5 | 5 | 5 | 5 | 5 | 5 |
| 93 | 400 | 3 | 2 | 4 | 5 | 5 | 5 |
| 94 | 400 | 4 | 1 | 4 | 5 | 5 | 5 |
| 95 | 400 | 4 | 3 | 4 | 5 | 5 | 5 |
| 96 | 400 | 5 | 5 | 5 | 5 | 5 | 5 |
| 97 | 400 | 2 | 1 | 5 | 5 | 5 | 5 |
| 98 | 400 | 5 | 4 | 5 | 5 | 5 | 5 |
| 99 | 400 | 1 | 1 | 1 | 5 | 5 | 4 |
| 100 | 400 | 5 | 5 | 5 | 5 | 5 | 5 |
| 101 | 400 | 5 | 5 | 5 | 5 | 5 | 5 |
| 102 | 400 | 5 | 5 | 5 | 5 | 5 | 5 |
| 103 | 400 | 5 | 5 | 5 | 5 | 5 | 5 |
| 104 | 400 | 5 | 5 | 5 | 5 | 5 | 5 |
| 105 | 400 | 5 | 5 | 5 | 5 | 5 | 5 |
| 106 | 400 | 5 | 5 | 5 | 5 | 5 | 5 |
| 107 | 400 | 5 | 5 | 4 | 5 | 5 | 5 |
| 108 | 400 | 5 | 5 | 5 | 5 | 5 | 5 |
| 109 | 400 | 5 | 5 | 5 | 5 | 5 | 5 |
| 110 | 400 | 5 | 5 | 5 | 5 | 5 | 5 |
| 111 | 400 | 5 | 5 | 5 | 5 | 5 | 5 |
| 112 | 400 | 5 | 5 | 5 | 5 | 5 | 5 |
| 113 | 400 | 5 | 5 | 4 | 5 | 5 | 5 |
| 114 | 400 | 5 | 5 | 5 | 5 | 5 | 5 |
| 115 | 400 | 5 | 5 | 5 | 5 | 5 | 5 |
| 116 | 400 | 5 | 5 | 5 | 5 | 5 | 5 |
| 117 | 400 | 5 | 5 | 5 | 5 | 5 | 5 |
| 118 | 400 | 4 | 4 | 5 | 5 | 5 | 4 |
| 119 | 400 | 5 | 4 | 5 | 5 | 5 | 2 |
| 120 | 400 | 2 | 2 | 5 | 5 | 5 | 1 |
| 121 | 400 | 5 | 3 | 5 | 5 | 5 | 5 |
| 122 | 400 | 5 | 5 | 5 | 5 | 5 | 5 |
| 123 | 400 | 5 | 5 | 5 | 5 | 5 | 5 |
| Comparative Compound A | 400 | 0 | 0 | 0 | 0 | 0 | 4 |
| Comparative Compound B | 400 | 0 | 0 | 0 | 0 | 1 | 5 |
| Comparative Compound C | 400 | 0 | 0 | 0 | 0 | 0 | 0 |

Note 1. The abbreviations of the tested plants are as follows (the same abbreviations may be used in other tables):
Ech: barnyardgrass (*Echinochloa crus-galli*)
Dig: crabgrass (*Digitaria sanguinalis*)
Pol: smartweed (*Polygonum lapathifolium*)
Ama: slender amaranth (*Amarathus viridis*)
Che: lambsquarters (*Chenopodium album*)
Cyi: rice flatsedge (*Cyperus iria*)

Note 2. Comparative Compounds A, B and C will be identified below (the same applies in other tables):
Comparative Compound A (disclosed in Japanese Unexamined Patent Publication No. 55729/1979)

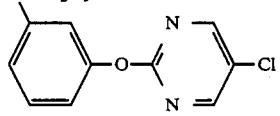

Comparative Compound B (disclosed in Japanese Unexamined Patent Publication No. 55729/1979)

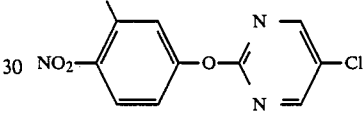

Comparative Compound C (disclosed in Arg. Biol. Chem., Vol. 30, No. 9,896 (1966))

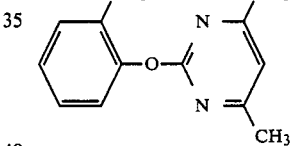

TEST EXAMPLE 2 (Foliage treatment)

In a 600 cm$^2$ pot filled with soil, seeds of barnyardgrass, crabgrass, smartweed, slender amaranth, lambsquarters and rice flatsedge, were sown, and covered with soil of a thickness of from 0.5 to 1 cm. The pot was cultured in a glass chamber at a temperature of from 20° to 25° C. for 2 weeks, and then a predetermined amount of a wettable powder prepared in accordance with Formulation Example 1 was diluted with water, and applied to the foliage at a rate of 100 liters per 10 ares. The evaluation was conducted on 14th day after the treatment with the herbicide. The results were evaluated in accordance with the standards as identified in Table 2, and shown by the index numbers in Table 4a and 4b.

TABLE 4-a

| Compound No. | Dose of active ingredient (g/10a) | Ech | Dig | Pol | Ama | Che | Cyi |
|---|---|---|---|---|---|---|---|
| 1 | 400 | 5 | 4 | 5 | 5 | 5 | 5 |
| 2 | 400 | 3 | 4 | 4 | 3 | 4 | 5 |
| 3 | 400 | 5 | 5 | 5 | 5 | 5 | 5 |
| 4 | 400 | — | — | 4 | 3 | 3 | 3 |
| 7 | 400 | 4 | 2 | 2 | 5 | 2 | 4 |
| 8 | 400 | 4 | 4 | 3 | 5 | 3 | 3 |
| 9 | 400 | 5 | 4 | 5 | 5 | 5 | 5 |

TABLE 4-a-continued

| Compound No. | Dose of active ingredient (g/10a) | Herbicidal effects | | | | | |
|---|---|---|---|---|---|---|---|
| | | Ech | Dig | Pol | Ama | Che | Cyi |
| 10 | 400 | 5 | 5 | 5 | 5 | 5 | 5 |
| 11 | 400 | 4 | 2 | 3 | 5 | 2 | 5 |
| 12 | 400 | 3 | 2 | 5 | 5 | 3 | 5 |
| 13 | 400 | 5 | 4 | 5 | 5 | 5 | 5 |
| 14 | 400 | 3 | 3 | 3 | 5 | 1 | 3 |
| 15 | 400 | 5 | 3 | 3 | 3 | 3 | 4 |
| 16 | 400 | 2 | 1 | 3 | 2 | 2 | 4 |
| 18 | 400 | 3 | 2 | 2 | 4 | 3 | 3 |
| 19 | 400 | 5 | 5 | 5 | 5 | 5 | 5 |
| 20 | 400 | 5 | 5 | 5 | 5 | 5 | 5 |
| 21 | 400 | 5 | 5 | 5 | 5 | 5 | 5 |
| 22 | 400 | 5 | 4 | 5 | 5 | 5 | 5 |
| 23 | 400 | 4 | 3 | 3 | 5 | 5 | 2 |
| 24 | 400 | — | — | 5 | 5 | 3 | 4 |
| 25 | 400 | 2 | 2 | 4 | 5 | 4 | 5 |
| 26 | 400 | 5 | 5 | 4 | 5 | 5 | 5 |
| 28 | 400 | 4 | 4 | 4 | 4 | 5 | 5 |
| 29 | 400 | 3 | 3 | 4 | 4 | 3 | 5 |
| 30 | 400 | 5 | 5 | 5 | 5 | 5 | 5 |
| 31 | 400 | 4 | 4 | 5 | 4 | 5 | 4 |
| 33 | 400 | 3 | 3 | 4 | 4 | 5 | 4 |
| 36 | 400 | 4 | 3 | 3 | 5 | 4 | 3 |
| 38 | 400 | 5 | 4 | 4 | 5 | 3 | 5 |
| 42 | 400 | 5 | 4 | 4 | 5 | 4 | 4 |
| 43 | 400 | 5 | 4 | 5 | 5 | 5 | 5 |
| 44 | 400 | 4 | 3 | 5 | 5 | 5 | 4 |
| 45 | 400 | 4 | 2 | 4 | 5 | 4 | 5 |
| 46 | 400 | 5 | 4 | 5 | 5 | 4 | 5 |
| 47 | 400 | 5 | 4 | 5 | 5 | 5 | 5 |
| 48 | 400 | 3 | 2 | — | 3 | 2 | 3 |
| 49 | 400 | 3 | 3 | 2 | 3 | 3 | 2 |
| 50 | 400 | 5 | 4 | 3 | 3 | 3 | 4 |
| 51 | 400 | 4 | 3 | 3 | 4 | 3 | 4 |
| 53 | 400 | 4 | 3 | 2 | 3 | 3 | 4 |
| 54 | 400 | 5 | 5 | 5 | 5 | 5 | 5 |
| 56 | 400 | 5 | 5 | 5 | 5 | 5 | 5 |
| 57 | 400 | 5 | 5 | 4 | 5 | 4 | 4 |
| 58 | 400 | 5 | 5 | 3 | 5 | 5 | 5 |
| 59 | 400 | 4 | 3 | 5 | 4 | 5 | 2 |
| 60 | 400 | 5 | 4 | 5 | 5 | 4 | 4 |
| 61 | 400 | 4 | 3 | 3 | 2 | — | 2 |
| 62 | 400 | 2 | 0 | 4 | 3 | 4 | 5 |
| 63 | 400 | 4 | 4 | 5 | 4 | 5 | 5 |
| 65 | 400 | 5 | 5 | 5 | 5 | 5 | 5 |
| 66 | 400 | 5 | 4 | 3 | 5 | 5 | 4 |
| 67 | 400 | 5 | 5 | 5 | 5 | 5 | 5 |
| 69 | 400 | 5 | 5 | 5 | 5 | 5 | 5 |
| 70 | 400 | 5 | 5 | 5 | 5 | 5 | 4 |
| 71 | 400 | 5 | 5 | 5 | 5 | 5 | 5 |
| 72 | 400 | 1 | 1 | 5 | 3 | 2 | 4 |
| 73 | 400 | 1 | 1 | 4 | 2 | 1 | 4 |
| 74 | 400 | 4 | 3 | 3 | 3 | 0 | 3 |
| 76 | 400 | 5 | 5 | 5 | 5 | 5 | 5 |
| 77 | 40 | 5 | 5 | 5 | 5 | 5 | 5 |
| 78 | 400 | 5 | 5 | 5 | 5 | 5 | 5 |
| Comparative Compound A | 400 | 0 | 1 | 2 | 2 | 0 | 5 |
| Comparative Compound B | 400 | 1 | 1 | 2 | 1 | 1 | 5 |
| Comparative Compound C | 400 | 1 | 1 | 1 | 1 | 1 | 1 |

TABLE 4-b

| Compound No. | Dose of active ingredient (g/10a) | Herbicidal effects | | | | | |
|---|---|---|---|---|---|---|---|
| | | Ech | Dig | Pol | Ama | Che | Cyi |
| 79 | 400 | 5 | 5 | 4 | 5 | 5 | 5 |
| 80 | 400 | 5 | 5 | 5 | 5 | 5 | 5 |
| 81 | 400 | 5 | 5 | 5 | 5 | 5 | 5 |
| 82 | 400 | 5 | 5 | 5 | 5 | 5 | 5 |
| 83 | 400 | 5 | 5 | 5 | 5 | 5 | 5 |
| 84 | 400 | 5 | 5 | 5 | 5 | 5 | 5 |
| 85 | 400 | 5 | 5 | 5 | 5 | 5 | 5 |
| 86 | 400 | 5 | 5 | 5 | 5 | 5 | 5 |
| 87 | 400 | 5 | 5 | 5 | 5 | 5 | 5 |
| 88 | 400 | 5 | 5 | 5 | 5 | 5 | 5 |
| 89 | 400 | 5 | 5 | 5 | 5 | 5 | 5 |
| 90 | 400 | 2 | 3 | 3 | 5 | 2 | 4 |
| 91 | 400 | 5 | 5 | 5 | 5 | 5 | 5 |
| 92 | 400 | 5 | 3 | 5 | 5 | 5 | 5 |
| 93 | 400 | 5 | 1 | 5 | 5 | 5 | 1 |
| 94 | 400 | 5 | 5 | 5 | 5 | 5 | 5 |
| 95 | 400 | 3 | 2 | 4 | 5 | 3 | 4 |
| 96 | 400 | 5 | 5 | 5 | 5 | 5 | 5 |
| 97 | 400 | 3 | 2 | 4 | 5 | 3 | 3 |
| 98 | 400 | 5 | 5 | 5 | 5 | 5 | 5 |
| 99 | 400 | 5 | 5 | 5 | 5 | 5 | 5 |
| 100 | 400 | 5 | 5 | 5 | 5 | 5 | 5 |
| 101 | 400 | 5 | 5 | 5 | 5 | 5 | 5 |
| 102 | 400 | 5 | 5 | 5 | 5 | 5 | 5 |
| 103 | 400 | 5 | 5 | 5 | 5 | 5 | 5 |
| 104 | 400 | 5 | 5 | 5 | 5 | 5 | 5 |
| 105 | 400 | 5 | 5 | 5 | 5 | 5 | 5 |
| 106 | 400 | 5 | 5 | 5 | 5 | 5 | 5 |
| 107 | 400 | 5 | 5 | 5 | 5 | 5 | 5 |
| 108 | 400 | 5 | 5 | 5 | 5 | 5 | 5 |
| 109 | 400 | 5 | 5 | 5 | 5 | 5 | 5 |
| 110 | 400 | 5 | 5 | 5 | 5 | 5 | 5 |
| 111 | 400 | 5 | 5 | 5 | 5 | 5 | 5 |
| 112 | 400 | 5 | 5 | 5 | 5 | 5 | 5 |
| 113 | 400 | 5 | 5 | 5 | 5 | 5 | 5 |
| 114 | 400 | 5 | 5 | 5 | 5 | 5 | 5 |
| 115 | 400 | 5 | 5 | 5 | 5 | 5 | 5 |
| 116 | 400 | 5 | 3 | 5 | 5 | 3 | 5 |
| 117 | 400 | 5 | 5 | 5 | 5 | 5 | 5 |
| 118 | 400 | 5 | 2 | 5 | 5 | 5 | 2 |
| 119 | 400 | 3 | 1 | 5 | 5 | 5 | 1 |
| 120 | 400 | 1 | 1 | 3 | 5 | 2 | 1 |
| 121 | 400 | 2 | 1 | 5 | 5 | 5 | 5 |
| 122 | 400 | 5 | 5 | 5 | 5 | 5 | 5 |
| 123 | 400 | 5 | 4 | 5 | 5 | 5 | 5 |
| Comparative Compound A | 400 | 0 | 0 | 2 | 1 | 0 | 4 |
| Comparative Compound B | 400 | 1 | 1 | 2 | 0 | 0 | 5 |
| Comparative Compound C | 400 | 0 | 1 | 1 | 1 | 0 | 1 |

TEST EXAMPLE 3 (effects against perennial weeds)

In a 600 cm$^2$ pot filled with soil, tubers of purple nutsedge and rhizomes of johnsongrass were planted and covered with soil of a thickness of from 0.5 to 1 cm. For the soil treatment, a predetermined amount of a wettable powder prepared in accordance with Formulation Example 1 was diluted with water and applied to the soil surface at a rate of 100 liters per 10 ares one day after the plantation. For the foliage treatment, the pot was cultured in a glass chamber at a temperature of from 20° to 25° C. for 2 weeks, and then a predetermined amount of a wettable powder prepared in accordance with Formulation Example 1 was diluted with water containing 2,000 ppm of surfactant wk as an extender and applied to the foliage at a rate of 100 liters per 10 ares. The evaluation was conducted on the 30th day after the treatment with the herbicide in the case of the soil treatment, and on the 21st day in the case of the foliage treatment. The results were evaluated in accordance with the standards as identified in Table 2 and shown by the index numbers in Table 5a, 5b, 5c and 5d.

TABLE 5-a (Soil treatment)

| Compound No. | Dose of active ingredient (g/10a) | Herbicidal effect Cyr | Sor |
|---|---|---|---|
| 1 | 400 | 2 | 5 |
| 3 | 400 | 5 | 5 |
| 9 | 400 | 4 | 3 |
| 12 | 400 | 5 | 4 |
| 13 | 400 | 5 | 5 |
| 19 | 400 | 5 | 5 |
| 26 | 400 | 5 | 5 |
| 30 | 400 | 5 | 5 |
| 43 | 400 | 5 | 5 |
| 46 | 400 | — | 5 |
| 54 | 400 | 4 | 5 |
| 56 | 400 | 5 | 5 |
| 57 | 400 | 5 | 5 |
| 63 | 400 | 5 | 5 |
| 65 | 400 | 5 | 5 |
| 67 | 400 | 4 | 5 |
| 69 | 400 | 5 | 5 |
| 70 | 400 | 5 | 5 |
| 76 | 400 | 5 | 5 |
| 77 | 400 | 5 | 5 |
| 78 | 400 | 5 | 5 |
| Comparative Compound A | 400 | 0 | 0 |
| Comparative Compound B | 400 | 0 | 0 |
| Comparative Compound C | 400 | 0 | 0 |

TABLE 5-b (Foliage treatment)

| Compound No. | Dose of active ingredient (g/10a) | Herbicidal effect Cyr | Sor |
|---|---|---|---|
| 1 | 400 | 4 | 5 |
| 3 | 400 | 5 | 5 |
| 9 | 400 | 4 | 5 |
| 13 | 400 | 4 | 5 |
| 19 | 400 | 5 | 5 |
| 26 | 400 | 4 | 5 |
| 28 | 400 | 4 | 4 |
| 30 | 400 | 5 | — |
| 43 | 400 | 5 | 5 |
| 45 | 400 | 4 | 4 |
| 47 | 400 | 3 | 4 |
| 54 | 400 | 4 | 5 |
| 65 | 400 | 5 | 5 |
| 69 | 400 | 4 | 5 |
| 76 | 400 | 5 | 5 |
| 77 | 400 | 5 | 5 |
| 78 | 400 | 5 | 5 |
| Comparative Compound A | 400 | 0 | 0 |
| Comparative Compound B | 400 | 0 | 0 |
| Comparative Compound C | 400 | 0 | 0 |

TABLE 5-c (Soil treatment)

| Compound No. | Dose of active ingredient (g/10 a) | Herbicidal effect Cyr | Sor |
|---|---|---|---|
| 80 | 100 | 5 | 5 |
| 81 | 100 | 5 | 5 |
| 82 | 100 | 5 | 5 |
| 85 | 100 | 5 | 5 |
| 87 | 100 | 5 | 5 |
| 89 | 100 | 5 | 4 |
| 91 | 100 | 4 | 5 |
| 96 | 100 | 5 | 5 |
| 98 | 100 | 5 | 5 |
| 100 | 400 | 4 | 5 |
| 101 | 100 | 5 | 5 |
| 102 | 400 | 5 | 5 |
| 104 | 100 | 5 | 5 |
| 105 | 100 | 5 | 5 |
| 106 | 400 | 4 | 5 |
| 108 | 100 | 5 | 5 |
| 112 | 100 | 5 | 5 |
| 115 | 100 | 5 | 5 |
| 117 | 100 | 5 | 5 |
| 121 | 400 | 5 | 5 |
| 123 | 100 | 5 | 5 |
| Comparative Compound A | 400 | 0 | 0 |
| Comparative Compound B | 400 | 0 | 0 |
| Comparative Compound C | 400 | 0 | 0 |
| Comparative Compound D | 400 | 1 | 0 |
| Comparative Compound D | 100 | 0 | 0 |

Comparative Compound D (disclosed in Japanese Unexamined Patent Publication No. 55729/1979)

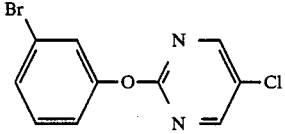

TABLE 5-d (Foliage treatment)

| Compound No. | Dose of active ingredient (g/10a) | Herbicidal effect Cyr | Sor |
|---|---|---|---|
| 79 | 400 | 5 | 5 |
| 80 | 100 | 5 | 5 |
| 82 | 100 | 5 | 5 |
| 84 | 100 | 4 | 5 |
| 85 | 100 | 5 | 5 |
| 86 | 100 | 5 | 5 |
| 89 | 100 | 5 | 5 |
| 91 | 100 | 5 | 5 |
| 92 | 400 | 4 | 5 |
| 94 | 100 | 5 | 5 |
| 95 | 100 | 5 | 5 |
| 96 | 100 | 5 | 5 |
| 98 | 100 | 5 | 5 |
| 99 | 100 | 5 | 5 |
| 100 | 100 | 5 | 5 |
| 103 | 400 | 5 | 5 |
| 106 | 100 | 5 | 5 |
| 109 | 100 | 5 | 5 |
| 110 | 100 | 4 | 4 |
| 111 | 100 | 4 | 5 |
| 113 | 400 | 5 | 5 |
| 114 | 100 | 5 | 4 |
| 117 | 100 | 5 | 5 |
| 121 | 100 | 4 | 5 |
| 122 | 400 | 5 | 5 |
| Comparative Compound A | 400 | 0 | 0 |
| Comparative Compound B | 400 | 0 | 0 |
| Comparative Compound C | 400 | 0 | 0 |
| Comparative Compound D | 400 | 1 | 1 |
| Comparative Compound D | 100 | 0 | 0 |

Note 1. The abbreviations of the tested plants are as follows (the same abbreviations are used in other tables).
Cyr: purpee nutsedge (*Cyperus rotundus*)(formation of tubers)
Sor: johnsongrass (*Sorghum halepense*)(formation of rhizomes)

TEST EXAMPLE 4 (safety to crop plants)

In 600 cm² pots filled with soil, seeds of annual weeds and crops, tubers of purple nutsedge and rhizomes of johnsongrass or bermudagrass, were sown or planted, respectively, and covered with soil of a thickness of from 0.5 to 1 cm. For the soil treatment, a predetermined amount of a wettable powder prepared in accordance with Formulation Example 1 was diluted with water and applied to the soil surface at a rate of 100 liters per 10 ares one day after the plantation. For the foliage treatment, the pot was cultured in a greenhouse for about 3 weeks, and then a predetermined amount of a wettable powder prepared in accordance with Formulation Example 1 was diluted with water and applied to the foliage at a rate of 100 liters per 10 ares. The evaluation was conducted on the 30th day after the treatment with the herbicide in the case of the soil treatment, and on the 21st day in the case of the foliage treatment. The evaluation of the herbicidal effects was conducted in accordance with the standards as identified in Table 2, and the evaluation of phytotoxicity was conducted in accordance with the standards as identified in Table 6. The results are shown by the index numbers in Tables 7a to 7e.

TABLE 6

| Index | Phytotoxicity |
|---|---|
| 0 | No phytotoxicity |
| 1 | Phytotoxicity more than 0% and less than 30% |
| 2 | Phytotoxicity at least 30% and less than 50% |
| 3 | Phytotoxicity at least 50% and less than 70% |
| 4 | Phytotoxicity at least 70% and less than 90% |
| 5 | Phytotoxicity at least 90% to completely withered |

TABLE 7-a (Soil treatment)

| Compound No. | Dose of active ingredient (g/10a) | Phytotoxicity Gly | Phytotoxicity Gos | Herbicidal effect Ech | Dig | Set | Pol | Ama | Sid | Sor |
|---|---|---|---|---|---|---|---|---|---|---|
| 1 | 400 | 0 | 1 | 5 | 4 | 5 | 5 | 5 | — | 5 |
| " | 100 | 0 | 0 | 4 | 3 | 5 | 5 | 5 | — | 5 |
| 46 | 400 | 2 | 2 | 5 | 5 | 5 | 5 | 5 | — | 5 |
| " | 100 | 1 | 1 | 5 | 4 | 5 | 5 | 5 | — | 3 |
| 54 | 400 | — | 1 | 5 | 5 | 5 | 5 | 5 | 5 | 5 |
| " | 100 | — | 0 | 5 | 5 | 5 | 5 | 5 | 3 | 5 |
| Comparative Compound A | 100 | 0 | 0 | 0 | 0 | 0 | 0 | 0 | 0 | 0 |
| Comparative Compound B | 100 | 0 | 0 | 0 | 0 | 0 | 0 | 0 | 0 | 0 |
| Comparative Compound C | 100 | 0 | 0 | 0 | 0 | 0 | 0 | 0 | 0 | 0 |

TABLE 7-b (Soil treatment)

| Compound No. | Dose of active ingredient (g/10a) | Phytotoxicity Gos | Herbicidal effects Ech | Pol | Cyr | Sor |
|---|---|---|---|---|---|---|
| 13 | 25 | 1 | 5 | 5 | 4 | 5 |
| " | 6.3 | 0 | 4 | 5 | 3 | 4 |
| 19 | 25 | 1 | 5 | 5 | 4 | 5 |
| " | 6.3 | 1 | 4 | 4 | 3 | 4 |
| 20 | 25 | 1 | 5 | 5 | 5 | 5 |
| " | 6.3 | 0 | 4 | 5 | 3 | 4 |
| 54 | 50 | 0 | 5 | 5 | — | 5 |
| " | 25 | 0 | 3 | 5 | — | 5 |
| 71 | 50 | 1 | 5 | 5 | 4 | 5 |
| " | 25 | 0 | 5 | 5 | 3 | 5 |
| 76 | 25 | 1 | 5 | 5 | 5 | 5 |
| " | 6.3 | 0 | 5 | 5 | 4 | 5 |
| 78 | 25 | 1 | 5 | 5 | 5 | 5 |
| " | 6.3 | 0 | 5 | 5 | 4 | 5 |
| 80 | 25 | 1 | 5 | 5 | 5 | 5 |
| " | 6.3 | 0 | 5 | 5 | 4 | 5 |
| 82 | 25 | 1 | 5 | 5 | 5 | 5 |
| " | 6.3 | 0 | 5 | 5 | 4 | 4 |
| 85 | 25 | 1 | 5 | 5 | 5 | 5 |
| " | 6.3 | 0 | 5 | 5 | 5 | 5 |
| 87 | 25 | 1 | 5 | 5 | 5 | 5 |
| " | 6.3 | 0 | 4 | 5 | 5 | 5 |
| 101 | 25 | 0 | 5 | 5 | 4 | 5 |
| 105 | 25 | 0 | 5 | 5 | 5 | 5 |
| Comparative Compound A | 25 | 0 | 0 | 0 | 0 | 0 |
| Comparative Compound B | 25 | 0 | 0 | 0 | 0 | 0 |
| Comparative Compound C | 25 | 0 | 0 | 0 | 0 | 0 |
| Comparative Compound D | 25 | 0 | 0 | 0 | 0 | 0 |

TABLE 7-c (Soil treatment)

| Compound No. | Dose of active ingredient (g/10a) | Phytotoxicity Gly | Herbicidal effects Set | Abt | Sor |
|---|---|---|---|---|---|
| 106 | 12.5 | 1 | 5 | 5 | 5 |
| " | 6.3 | 0 | 4 | 4 | 4 |
| Comparative Compound D | 12.5 | 0 | 0 | 0 | 0 |

TABLE 7-d (Foliage treatment)

| Compound No. | Dose of active ingredient (g/10a) | Phytotoxicity Tri | Herbicidal effects Ste | Rap | Pol | Ama |
|---|---|---|---|---|---|---|
| 123 | 3 | 0 | 4 | 5 | 5 | 5 |
| " | 1 | 0 | 3 | 4 | 4 | 3 |
| Comparative Compound D | 3 | 0 | 0 | 0 | 0 | 0 |
| Comparative Compound D | 1 | 0 | 0 | 0 | 0 | 0 |

TABLE 7-e

| | | (Soil treatment) | | | | | | |
|---|---|---|---|---|---|---|---|---|
| Compound No. | Dose of active ingredient (g/10a) | Phytotoxicity Hel | Herbicidal effects | | | | | |
| | | | Ech | Set | Cyr | Soh | Cyd |
| 19 | 25 | 1 | 5 | 5 | 5 | 5 | 4 |
| " | 6.3 | 1 | 4 | 5 | 4 | 5 | 3 |
| Comparative Compound D | 25 | 0 | 0 | 0 | 0 | 0 | 0 |

Note 1. Abbreviations for the tested plants are as follows.
Gly: soybean (*Glycine max*)
Gos: cotton (*Gossypium hirsutum*)
Hel: sunflower (*Helianthus annus*)
Tri: wheat (*Triticum aestivum*)
Ech: barnyardgrass (*Echinochlca crus-galli*)
Dig: crabgrass (*Digitaria sanguinalis*)
Set: greenfoxtail (*Setaria viridis*)

We claim:

1. A 2-phenoxypyrimidine derivative having the formula:

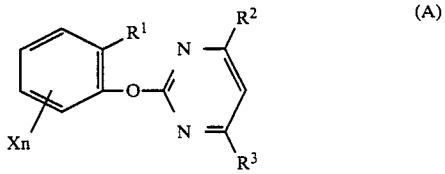

(A)

wherein $R^1$ is —COOR$^4$, wherein $R^4$ is hydrogen, lower alkyl or benzyl, each of groups $R^2$ and $R^3$ is methoxy, and X is lower alkyl, lower alkoxy, halogen or nitro, and n is 1 or 2.

2. The 2-phenoxypyrimidine derivative according to claim 1, wherein n is 2, and one X is located at 6-position and another X is located at 3-, 4- or 5-position.

3. The 2-phenoxypyrimidine derivative according to claim 1, wherein n is 1, and X is located at 3-, 4-, 5- or 6-position.

4. The 2-phenoxypyrimidine derivative according to claim 3, wherein X is a halogen atom, a lower alkyl group or a lower alkoxy group.

5. The 2-phenoxypyrimidine derivative according to claim 1, wherein n is 2, each of two X which may be the same or different, is a halogen atom or a methyl group, $R^1$ is —COOH, and each of $R^2$ and $R^3$ is a methoxy group.

6. The 2-phenoxypyrimidine derivative according to claim 1, wherein n is 1, X is a halogen atom or a lower alkoxy group at 3-, 4-, 5- or 6-position, $R^1$ is —COOR (wherein R is a hydrogen atom or a $C_1$-$C_5$ alkyl group), and each of $R^2$ and $R^3$ is a methoxy group.

7. The 2-phenoxypyrimidine derivative according to claim 6, wherein X is located at 6-position.

8. The 2-phenoxypyrimidine derivative according to claim 6 or 7, wherein X is a chlorine atom.

9. The 2-phenoxypyrimidine derivative according to claim 1, which is 2-fluoro-6-(4,6-dimethoxypyrimidin-2-yl)oxy benzoic acid, 2-chloro-6-(4,6-dimethoxypyrimidin-2-yl)oxy benzoic acid, methyl 2-chloro-6-(4,6-dimethoxypyrimidin-2-yl)oxy benzoate, ethyl 2-chloro-6-(4,6-dimethoxypyrimidin-2-yl)oxy benzoate, benzyl 2-chloro-6-(4,6-dimethoxypyrimidin-2-yl)oxy benzoate, 2-ethoxy-6-(4,6-dimethoxypyrimidin-2-yl)oxy benzoic acid, isobutyl 2-chloro-6-(4,6-dimethoxypyrimidin-2-yl)oxy benzoate, n-butyl 2-chloro-6-(4,6-dimethoxypyrimidin-2-yl)oxy benzoate, 2-bromo-6-(4,6-dimethoxypyrimidin-2-yl)oxy benzoic acid or n-propyl 2-chloro-6-(4,6-dimethoxypyrimidin-2-yl)oxy benzoate.

10. A herbicidal composition comprising a herbicidally effective amount of a 2-phenoxypyrimidine derivative as defined in claim 1 and an agricultural adjuvant.

11. A method for killing weeds which comprises applying a herbicidally effective amount of a 2-phenoxypyrimidine derivative as defined in claim 1 to a locus to be protected.

* * * * *